US011896195B2

(12) United States Patent
Thomas et al.

(10) Patent No.: US 11,896,195 B2
(45) Date of Patent: Feb. 13, 2024

(54) DISTRIBUTED IMAGE PROCESSING SYSTEM IN OPERATING THEATER

(71) Applicant: Sony Corporation, Tokyo (JP)

(72) Inventors: Alexander Thomas, Stuttgart (DE);
Sander Brandenburg, Stuttgart (DE);
Joris Guisson, Stuttgart (DE); Erik Cumps, Stuttgart (DE); Robert Koninckx, Stuttgart (DE)

(73) Assignee: SONY CORPORATION, Tokyo (JP)

( * ) Notice: Subject to any disclaimer, the term of this patent is extended or adjusted under 35 U.S.C. 154(b) by 492 days.

(21) Appl. No.: 17/260,550

(22) PCT Filed: Jul. 24, 2019

(86) PCT No.: PCT/EP2019/069948
§ 371 (c)(1),
(2) Date: Jan. 15, 2021

(87) PCT Pub. No.: WO2020/020959
PCT Pub. Date: Jan. 30, 2020

(65) Prior Publication Data
US 2021/0274998 A1 Sep. 9, 2021

(30) Foreign Application Priority Data
Jul. 24, 2018 (EP) .................... 18185365

(51) Int. Cl.
*A61B 1/00* (2006.01)
*A61B 90/00* (2016.01)
*A61B 1/045* (2006.01)

(52) U.S. Cl.
CPC ........ *A61B 1/00004* (2013.01); *A61B 1/0005* (2013.01); *A61B 1/00013* (2013.01);
(Continued)

(58) Field of Classification Search
CPC .......... A61B 1/00004; A61B 1/000095; A61B 1/00013; A61B 1/0005; A61B 1/045; A61B 90/37
See application file for complete search history.

(56) References Cited

U.S. PATENT DOCUMENTS 9,264,663 B2    2/2016  Koninckx et al.
10,555,393 B1 *  2/2020  Fu ....................... F21V 33/0052
(Continued)

FOREIGN PATENT DOCUMENTS

EP      3029934 A1    6/2016
JP    2008253586 A   10/2008
(Continued)

OTHER PUBLICATIONS

International Search Report and Written Opinion dated Nov. 11, 2019, received for PCT Application No. PCT/EP2019/069948 Filed on Jul. 24, 2019, 9 pages.
(Continued)

*Primary Examiner* — Brian P Yenke
(74) *Attorney, Agent, or Firm* — XSENSUS LLP (57) ABSTRACT

A processing system (100, 200) for processing surgical images. The system includes at least one image pickup unit (115) for obtaining surgical image frames and data, at least one image receptor (113) for receiving surgical image frames to be displayed, and a processing unit (153) connected with a network (103, 106, 107) to the image pickup unit (115) for receiving surgical image frames, the processing unit (153) being configured for processing the surgical image frames and for extracting at least one processing information thereof. The processing unit further is being connected to the at least one image receptor (113) for providing the at least one correction parameter to the at least one image receptor. The system further comprises a connection (102) between the at least one image pickup unit (Continued)

(115) and the image receptor (113), for sending the surgical image frames directly to the image receptor (113).

17 Claims, 5 Drawing Sheets (52) U.S. Cl.
CPC ........ *A61B 1/000095* (2022.02); *A61B 1/045* (2013.01); *A61B 90/37* (2016.02)

(56) References Cited

U.S. PATENT DOCUMENTS

| | | | | |
|---|---|---|---|---|
| 2005/0033117 | A1* | 2/2005 | Ozaki | A61B 5/1076 600/117 |
| 2014/0267812 | A1* | 9/2014 | Kennedy | A61B 1/00016 348/211.3 |
| 2015/0078615 | A1* | 3/2015 | Staples, II | G06T 7/50 382/103 |
| 2016/0174823 | A1* | 6/2016 | Asatori | A61B 1/00042 348/49 |
| 2016/0338590 | A1* | 11/2016 | Sagalovich | A61B 1/07 |
| 2018/0168740 | A1* | 6/2018 | Ryan | A61B 90/36 |
| 2018/0168769 | A1* | 6/2018 | Wood | A61B 1/00188 |
| 2019/0201143 | A1* | 7/2019 | Shelton, IV | A61B 17/07207 |
| 2019/0201145 | A1* | 7/2019 | Shelton, IV | G16H 20/30 |
| 2019/0289284 | A1* | 9/2019 | Smith | A61B 1/00193 |
| 2020/0041261 | A1* | 2/2020 | Bernstein | A61B 90/30 |
| 2021/0015432 | A1* | 1/2021 | Konno | A61B 5/02042 |
| 2021/0196425 | A1* | 7/2021 | Shelton, IV | A61B 90/30 |
| 2022/0086393 | A1* | 3/2022 | Peters | G06V 20/41 |
| 2022/0217286 | A1* | 7/2022 | Osborne | A61B 5/066 |
| 2022/0392617 | A1* | 12/2022 | Asai | G16H 40/20 |
| 2023/0133330 | A1* | 5/2023 | Hawkins | G16H 40/20 705/2 |

FOREIGN PATENT DOCUMENTS

| | | |
|---|---|---|
| JP | 2014003990 A | 1/2014 |
| JP | 2014008126 A | 1/2014 |
| JP | 2014128423 A | 7/2014 |
| WO | 2017/002380 A1 | 1/2017 |
| WO | 2017/056762 A1 | 4/2017 |

OTHER PUBLICATIONS

Alizadeh et al., "Effects of Improved Adaptive Gamma Correction Method on Wireless Capsule Endoscopy Images: Illumination Compensation and Edge Detection", 20th Iranian Conference on Electrical Engineering (ICEE 2012), IEEE, May 15-17, 2012, pp. 1544-1548.

Nucleus, The Smart Digital Operating Room, Saturnus, 16 pages.

Fastvideo, "Software for Image Enhanced Endoscopy (IEE)", 1 page.

* cited by examiner

DISTRIBUTED IMAGE PROCESSING SYSTEM IN OPERATING THEATER

TECHNICAL FIELD OF THE INVENTION

The present invention relates to the field of image processing. More specifically, it relates to video data communication and processing systems, as well as methods of communication and video data processing.

The present application claims the Paris Convention priority of European Patent Application no. 18185365.6, the contents of which are hereby incorporated by reference.

BACKGROUND OF THE INVENTION

Some types of surgery are performed by inserting instruments for aiding the visualization of the region to be operated. For example, endoscopes can be introduced in the body and acquire images, as a video streaming, which are displayed on an external display.

The nature of the surgical process allows little margin of error. The video streaming usually needs corrections and adjustments. For example, the amount of light received by the scope may change, and the video display should compensate for these changes. Color correction may also be required.

However, complex video, image and data processing techniques, although they provide corrections and adjustments, they introduce latency on the video stream. The surgeon may lose coordination and reference of the relative position of the instruments and the operation region, which creates dangerous situations.

Moreover, the computing power required to process digital video images is considerable, especially if required to process them in real time. This is not always welcome in an operating theater, because such computing power usually requires space and/or creates obstacles in the theater, and produces noise.

Although currently various types of image processing, such as for example image quality enhancement, making annotations to visualize the surgical process, and AI-based diagnosis, are being developed, such functions cannot be implemented onto a processor located in the operating theater because it is not easy to update or enhance the functions of the processor and because processors in the operating theater are required to have a small footprint.

SUMMARY OF THE INVENTION

It is an object of embodiments of the present invention to provide a video and image processing system suitable for use during surgery, as well as a method for processing video and image data, while allowing image and video streaming with no latency.

The present invention relates to a processing system for processing surgical images, the system including:
  at least one image pickup unit for obtaining surgical image frames and data,
  at least one image receptor for receiving surgical image frames to be displayed,
  a processing unit connected with a network to the image pickup unit for receiving surgical image frames, the processing unit being configured for processing the surgical image frames and for extracting at least one processing information, e.g. a correction parameter, thereof, wherein the processing unit further is being connected to the at least one image receptor for providing the processing information to the at least one image receptor, and wherein the system further comprises a connection between the at least one image pickup unit and the image receptor, for sending the surgical image frames directly to the image receptor.

It is an advantage of embodiments of the present invention that data processing can be provided simultaneously to real time image display, thus reducing or avoiding latency in the output (e.g. in a display) while still allowing image processing and correction.

The processing unit may be an external processing unit positioned outside an operation theater separated from the at least one image pickup unit and the at least one image receptor positioned inside the operation theater. It is an advantage of embodiments of the present invention that data processing can be provided outside an operation theater, thus allowing enough room and reducing noise in the theater.

The processing unit may be adapted to provide processing information from surgical image frames and further image data, the processing unit further including input for receiving further image data. It is an advantage of embodiments of the present invention that further information from conditions of image acquisition can be taken into account.

The at least one image receptor may include means for applying at least processing information, e.g. one correction parameter, to image frames. It is an advantage of embodiments of the present invention that data processing and corrections can be applied to frames of image data, and only the parameters need to be transmitted rather than whole images, which reduces latency.

The at least one image pickup unit may comprise a surgical video input and the image frames comprise a surgical video stream. It is an advantage of embodiments of the present invention that standardized video inputs (e.g. cameras) and video processing can be applied, and corrections can be applied to the video streaming with very little or without appreciable latency.

The image receptor may include a display for displaying surgical image frames. It is an advantage of embodiments of the present invention a surgeon can follow a surgery process in real time, for example by video streaming.

The at least one image pickup unit may comprise an endoscope. It is an advantage of embodiments of the present invention that image data processing can be applied during standard endoscopic surgery without appreciable image latency.

The system may b connected via Gigabit Ethernet. It is an advantage of embodiments of the present invention that the use of Gigabit Ethernet allows achieving low latency transmission.

Image data transmitted in the system may be transmitted in a slice based transmission mode.

Image data transmitted in the system may be compressed prior to transmission. The compression may be wavelet based compression.

The present invention also relates to a method for processing images comprising
  obtaining surgical image frames,
  sending at least one surgical image frame to an image receptor,
  separately processing the at least one surgical image frame thereby extracting processing information, e.g. at least one correction parameter,
  subsequently adjusting any further surgical image frames sent to the image receptor by applying the processing information, e.g. at least one correction parameter, to the any further surgical image frames. It is an advantage of embodiments of the present invention that the processing of frames is performed independently to sending the image frames to the receptor, so the step of sending the frames to an output is not delayed by image processing.

It is an advantage of embodiments of the present invention that the image can be sent to the readout and simultaneously any processing information, e.g. correction parameter, extracted separately from a previous image frame can be applied with little or no appreciable delay to subsequent image frames.

The method further may comprise displaying the surgical image frames received in the image receptor. It is an advantage of embodiments of the present invention that corrected image frames can be displayed in a monitor, screen, overhead projector, portable device and the like, with little or no appreciable delay.

The method further may comprise obtaining image data, and wherein processing the surgical image frames and extracting at least one processing information comprises processing the surgical image frames and image data related to the conditions of obtaining surgical image frames.

It is an advantage of embodiments of the present invention that image acquisition conditions can be taken into account in the correction.

Obtaining surgical image frames may comprise obtaining a surgical video stream.

Extracting at least one processing information may include extracting any or all of color correction, contrast correction, illumination information, displacement and image rotation.

The present invention also relates to a processing unit for processing surgical images, the processing unit being configured for receiving surgical image frames and data from at least one image pickup unit for obtaining surgical image frames and data, processing the surgical image frames and for extracting at least one processing information thereof, and providing the at least one processing information to at least one image receptor for applying said at least one processing information to surgical image frames received by the at least one image receptor directly from the at least one image pickup unit.

The present invention furthermore relates to an image receptor for receiving surgical image frames to be displayed, the image receptor being configured for receiving surgical image frames directly from at least one image pickup unit and for receiving an at least one processing information, e.g. a correction parameter, determined by a processor based on surgical image frames received from said at least one image pickup unit (115), the image receptor being configured for applying the at least one processing information to the surgical image frames received directly from the at least one image pickup unit.

Particular and preferred aspects of the invention are set out in the accompanying independent and dependent claims. Features from the dependent claims may be combined with features of the independent claims and with features of other dependent claims as appropriate and not merely as explicitly set out in the claims. These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes. Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein. Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Figure 1:
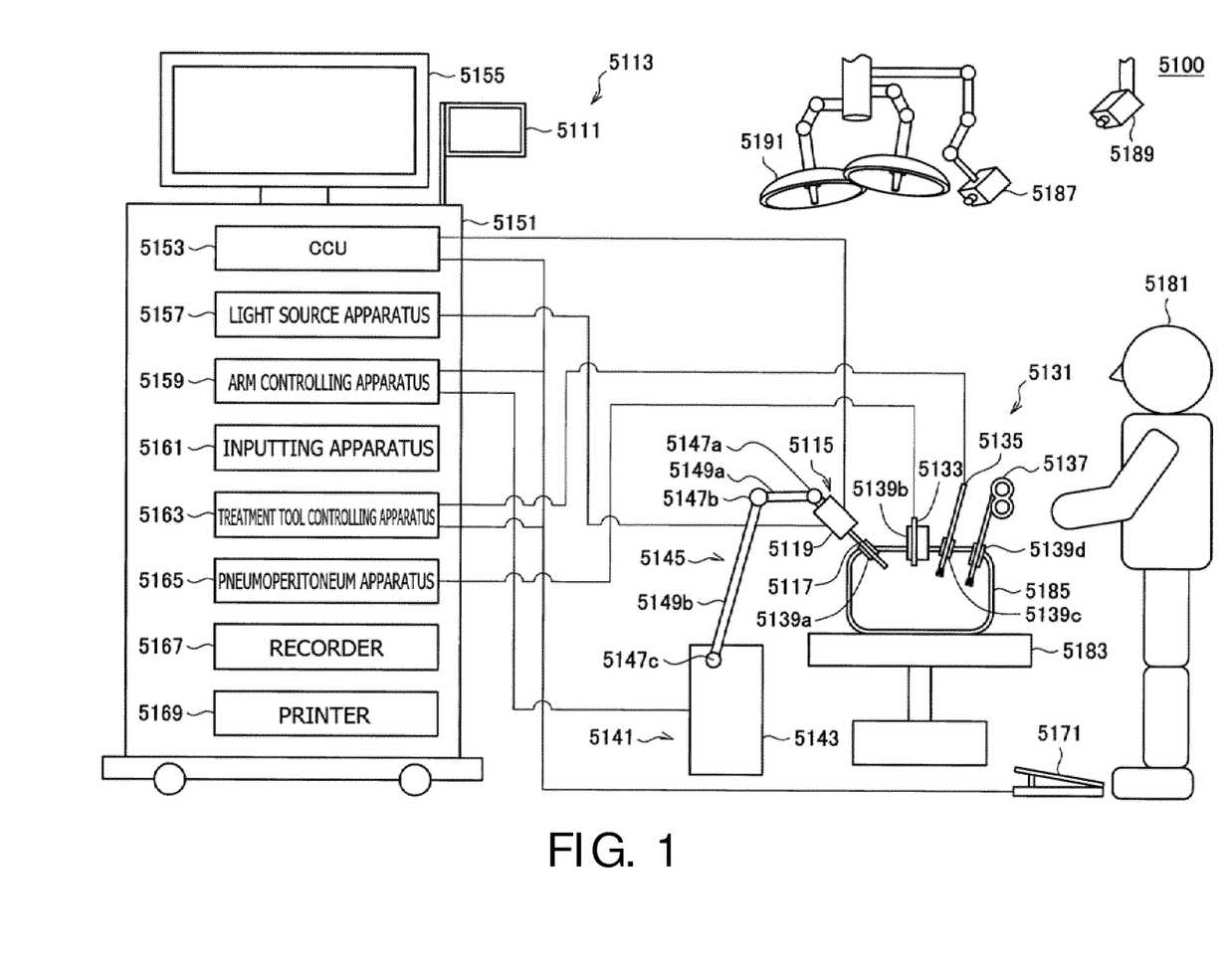
FIG. 1 is a view illustrating an example of a state of surgery according to existing surgery room systems.

By way of illustration, the context for which the image processing according to embodiments of the present invention are described, will be illustrated by the description of an exemplary operating theater and imaging system (in the present example an endoscopic system). It will be clear that this is only given by way of illustrating the context of embodiments of the present invention, but that these embodiments are also applicable to other types of operating theaters and to other types of imaging systems. FIG. 1 is a view illustrating an example of a state of surgery applied to a surgery room system according to the prior art. A ceiling camera 5187 and a surgery field camera 5189 are provided on the ceiling of the surgery room such that it can image the hands of a surgeon (medical doctor) 5181 who performs treatment for an affected area of a patient 5185 on a patient bed 5183 and the entire surgery room. The ceiling camera 5187 and the surgery field camera 5189 may include adjustment functions (magnification, focal distance, and so forth). An illumination 5191 is provided on the ceiling of the surgery room and irradiates at least upon the hands of the surgeon 5181. The illumination 5191 may be configured such that the irradiation light amount, the wavelength (color) of the irradiation light, the irradiation direction of the light and so forth can be adjusted suitably.

The endoscopic surgery system 5113, the patient bed 5183, the ceiling camera 5187, the surgery field camera 5189 and the illumination 5191 can be connected for cooperation with each other, e.g. through an audiovisual controller and a surgery room controlling apparatus. A centralized operation panel 5111 can provided in the surgery room, and the user can suitably operate the apparatus existing in the surgery room through the centralized operation panel 5111.

Still referring to FIG. 1, a configuration of an endoscopic surgery system 5113 is described in detail. It includes an endoscope 5115, other surgical tools 5131, a supporting arm apparatus 5141 which supports the endoscope 5115 thereon, and a cart 5151 on which various apparatus for endoscopic surgery are mounted.

In endoscopic surgery, in place of incision of the abdominal wall to perform laparotomy, a plurality of tubular aperture devices called trocars 5139a to 5139d can be used to puncture the abdominal wall. Then, a lens barrel 5117 of the endoscope 5115 and the other surgical tools 5131 are inserted into body lumens of the patient 5185 through the trocars 5139a to 5139d. In the example depicted, as the other surgical tools 5131, a pneumoperitoneum tube 5133, an energy treatment tool 5135 (for performing incision, peeling, sealing vessels or the like by high frequency current or ultrasonic vibration) and forceps 5137 are inserted into body lumens of the patient 5185. However, the surgical tools 5131 depicted are mere examples. Various surgical tools which are generally used in endoscopic surgery such as, for example, a pair of tweezers or a retractor may be used.

An image of a surgical region in a body lumen of the patient 5185 picked up by the endoscope 5115 can be displayed on a display apparatus 5155. A pneumoperitoneum apparatus 5165 can be used to feed gas into a body lumen of the patient 5185 through the pneumoperitoneum tube 5133 to inflate the body lumen in order to secure the field of view of the endoscope 5115 and secure the working space for the surgeon. The surgeon 5181 can use the energy treatment tool 5135 or the forceps 5137 while watching the image of the surgical region displayed on the display apparatus 5155 to perform such treatment as, for example, resection of an affected area.

The endoscope 5115 may include a lens barrel 5117 which has a region of a predetermined length from a distal end thereof to be inserted into a body lumen of the patient 5185, and a camera head 5119 connected to a proximal end of the lens barrel 5117. The endoscope 5115 of FIG. 1 is depicted as a hard mirror having the lens barrel 5117 of the hard type, but the endoscope 5115 may otherwise be configured as a soft mirror having the lens barrel 5117 of the soft type.

The lens barrel 5117 has, at a distal end thereof, an opening in which an objective lens is fitted. A light source apparatus 5157 is connected to the endoscope 5115 such that light generated by the light source apparatus 5157 is introduced to a distal end of the lens barrel 5117 by a light guide extending in the inside of the lens barrel 5117 and is applied toward an observation target in a body lumen of the patient 5185 through the objective lens. The endoscope 5115 may be a direct view mirror or may be a perspective view mirror or a side view mirror.

(Camera Head and CCU)

An optical system and an image pickup element are provided in the inside of the camera head 5119 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal can be transmitted as RAW data to a camera control unit (CCU) 5153. The camera head 5119 may have a function incorporated therein for suitably driving the optical system of the camera head 5119 to adjust the magnification and the focal distance.

The CCU 5153 may include a central processing unit (CPU), a graphics processing unit (GPU) or the like and may integrally control operation of the endoscope 5115 and/or the display apparatus 5155. For example the CCU 5153 performs, for an image signal received from the camera head 5119, various image processes for displaying an image based on the image signal such as, for example, a development process (demosaic process). The CCU 5153 provides the image signal for which the image processes have been performed to the display apparatus 5155. The CCU 5153 may be connected to an audiovisual controller and provide the image signal for which the image processes have been performed.

Further, the CCU 5153 may include a communication unit for transmitting a control signal to the camera head 5119 to control driving of the camera head 5119. The control signal may include information relating to an image pickup condition such as information that a frame rate of a picked up image is designated, information that an exposure value upon image picking up is designated and/or information that a magnification and a focal point of a picked up image are designated. Further, the camera head 5119 may include a communication unit for receiving a control signal for controlling driving of the camera head 5119 from the CCU 5153. The communication unit provides the received control signal to a camera head controlling unit 5129.

It is to be noted that the image pickup conditions such as the frame rate, exposure value, magnification or focal point can be set automatically by the CCU 5153 (e.g. by a control unit 5177 thereof) on the basis of an acquired image signal. In other words, an auto exposure (AE) function, an auto focus (AF) function and an auto white balance (AWB) function can be incorporated in the endoscope 5115.

Complex digital video, image and data processing techniques can bring a lot of added value to surgeons and other health care professionals in operating theaters. These digital techniques bring benefit to or improve the clinical decisions made by these health care professionals, and improve safety and quality in the operating theater. However, complex video, image and data processing techniques usually introduce latency on the video stream. Moreover, they require computing power which is not always welcome in an operating theater.

Specifically, digital video, image and data processing techniques can be performed in the CCU 5153 as shown in FIG. 1, but these techniques require processing time, which introduces additional latency on the display of image frames in a stream (e.g. endoscopic video stream) which is used by the surgical staff to perform the surgical procedure. For example, the images may be displayed with a delay with respect of the actual motions of the devices, and/or video needs a buffering time. This may disturb the surgeon's hand-eye coordination.

Moreover, for complex image data, computing power provided of the CCU is provided by noisy, actively cooled, computing machines which are typically not welcome inside the operating theater. For example, the CCU may require active cooling with a fan inside the computing machine, which generates noise which may be disturbing during an operation. They also occupy space in the operating theater as shown in FIG. 1, and they require appropriate maintenance procedures to avoid dust collection.

The present invention relates to a distributed image processing system and method suitable for processing images related to surgery, where the stream of image data (e.g. the video stream) obtained with an image pickup element can be directly sent to an image receptor (e.g. a display for viewing the images) with low latency, and it is also sent to a processing unit. The processing unit can extract processing information, e.g. correction parameters, from the stream of image data, including an image itself and data regarding the pickup conditions, or conditions under which the image stream is acquired by the image pickup unit.

In embodiments of the present invention, the distributed image processing provides digital video, image and data processing techniques and its related computing power outside the operating theater. Thus, a processing unit is provided outside the operating theater, reducing noise therein and allowing more space. The processing unit may include a computing machine, CPU or the like for analysis of the stream of image frames and/or image data.

Figure 2:
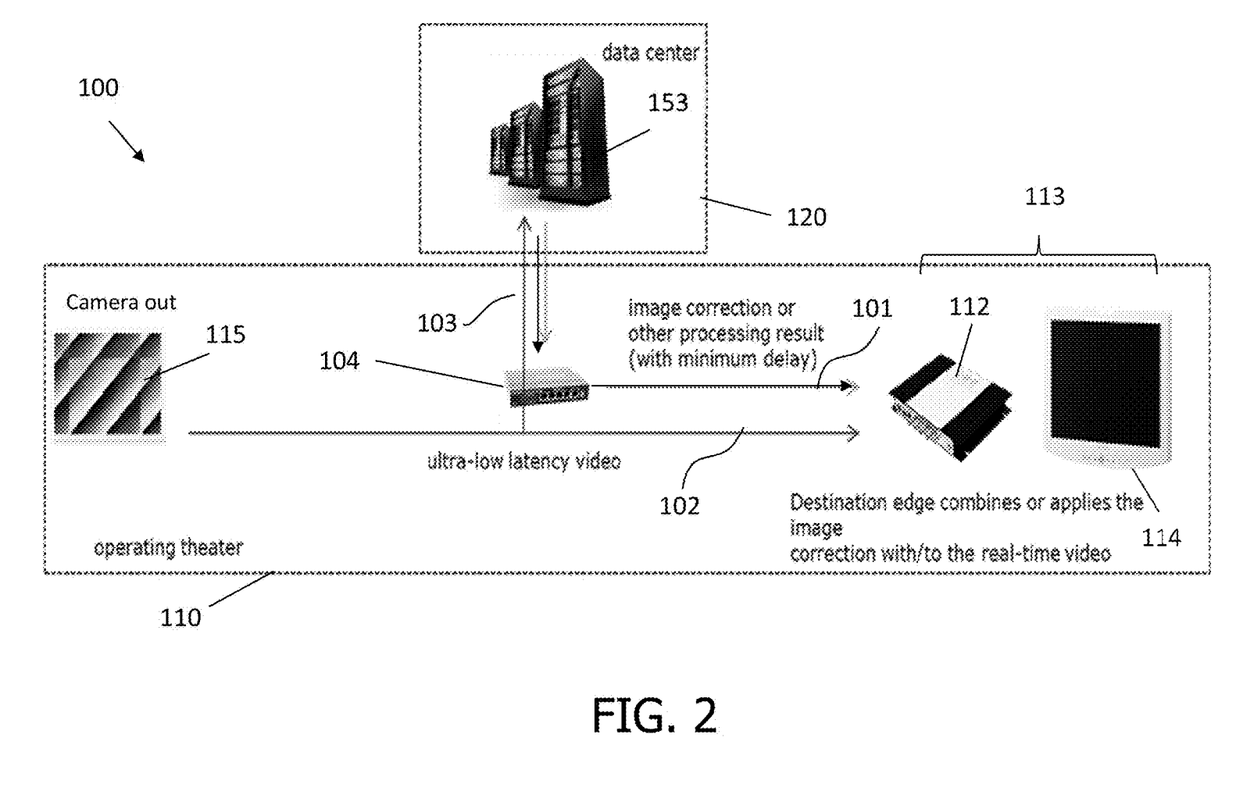
FIG. 2 is a view illustrating an example of a distributed image processing according to embodiments of the present invention.

In a first aspect, the present invention provides a system for processing image frames obtained for example during surgery. FIG. 2 shows a distributed processing system 100 according to embodiments of the present invention comprising an operating theater 110 including an image pickup unit 115 (which may include, for example, an endoscope), a data transmission or network medium 101, 102, 103 which may include a distributing node 104, and an image receptor 113. A data center 120 includes a processing unit 153. The data center 120 is external to the operating theater 110. For example, the data center 120 may be or be included in a centralized computer system of a surgery center, clinic, hospital, or the like, physically separated from the operating theaters. This has the simultaneous advantages that more space is provided to the operating theaters, less noise is introduced there from the operation of the computer system (e.g. from cooling of the processing unit 153). Further, dedicated maintenance can be provided to the system in the separate data center 120, with no influence on the operating theater 110.

The image pickup unit 115 may comprise an optical detector, for example a sensor, for obtaining an image frame. For example, a pixel array can be used, including for instance photoelectric elements, CMOS-type sensors, or the like. Other elements relating to optics (lenses, apertures, and the like) and to electronics (charge-to-voltage converters, and the like) may be included.

In some embodiments, the image pickup unit 115 may comprise an endoscope 5115 as discussed with reference to FIG. 1. It may include a video input, for example. It may include one or more image pickup elements. It is to be noted that, in order to establish compatibility with, for example, a stereoscopic vision (3D display), a plurality of image pickup elements may be provided on the camera head 5119 of an endoscope 5115 as. In this case, a plurality of relay optical systems can be provided in the inside of the lens barrel 5117 to guide observation light to the plurality of respective image pickup elements.

However, the present invention is not limited to one endoscope, and it may include more than one. Also, the present invention is not limited to endoscopes, and any other image pickup unit (e.g. surgery microscopes) can be used, for providing image frames (e.g. a video stream) and image data. The image data is related to the image frame, and it can be extracted therefrom. Additionally, further image data can be extracted from conditions in which the image frame has been taken (refresh rate, illumination, and the like), which can be included as additional separate image data. Thus, the system of the present invention may comprise other elements (e.g. illumination systems 5191, light source apparatus 5157 as shown in FIG. 1, and the like) from which further image data can be obtained.

The image data that is transmitted, can be RAW image data (non-compressed image data) or compressed image data to reduce the size of the data. An example of image coded for transmission is a low latency video codec (LLVC). According to this codec, the image data is transmitted whereby the image data is divided into a plurality of image slices. It can be compressed by using wavelet based image compression.

The network used for transmitting may be Gigabit Ethernet. For some part of the network wireless communication can be employed.

The processing unit 153 of the present invention may comprise one or more central processing unit (CPU), graphics processing unit (GPU) or the like. When the processor operates in accordance with a predetermined program, the image processes and the detection process of the present invention can be performed. It is to be noted that, where the processing unit 153 includes a plurality of GPUs, the processing unit 153 suitably divides information relating to an image signal such that image processes are performed in parallel by the plurality of GPUs.

The processing unit 153 may be equipped with connections and inputs to obtain further image data related to image pickup conditions such as the frame rate, exposure value, magnification or focal point, and the like. Thus, the CCU 5153 of the prior art system of FIG. 1 can be relieved of many processing burdens, such as image analysis or some aspects of camera control. In some embodiments, the CCU may be located outside the operating theater. In some embodiments, the presence of a CCU is not needed, and any image process and analysis can be performed by the processing unit 153, e.g. by the centralized processing unit in a data center 120.

The image receptor 113 of the present invention may comprise a device for receiving both image frames from the image pickup unit and data processed by a processing unit, particularly processing information, e.g. correction parameters, extracted by the processing unit 153. The image receptor may comprise one or more output devices for outputting the image frames received. For example, the image receptor 113 may comprise displays such as screens or projectors, or a printer 5169 and/or recorder 5167 such as the ones shown in FIG. 1. In preferred embodiments, the image receptor 113 comprises at least one display 114, for example a monitor, screen, overhead projector or the like for showing image frames, for assistance of a medical team during surgery, laparoscopy, or the like.

For example, the display 114 may display image frames, for example as a video stream, provided by the at least one image pickup unit 115. The signal may be pre-processed (e.g. by a CCU 5153 as shown in FIG. 1), but in preferred embodiments the pre-processing is minimal. For example, the display 114 may directly display images directly from the image pickup elements (such as RAW images), or directly the video signal. Hence, display of image frames can be done with no latency. If the image pickup unit 115 (e.g. an endoscope) is ready for imaging of a high resolution such as 4K (horizontal pixel number 3840×vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus. Where the apparatus is ready for imaging of a high resolution such as 4K or 8K, if the display apparatus used as the display 114 has a size of equal to or not less than 55 inches, then a more immersive experience can be obtained. Further, a plurality of display apparatus having different resolutions and/or different sizes may be provided in accordance with different purposes.

The image receptor 113 also receives data (including correction parameters, as mentioned earlier) from the processing unit with minimum delay. The image receptor 113 displays corrected image frames by applying corrections, based on the received processing information, e.g. correction parameters, calculated from previous image frames, to the received image frames (e.g. to the video stream). For example, the image receptor 113 may include an image corrector 112, which may comprise a further processing unit, for example a small processor or GPU which can apply the correction based on the processing information, e.g. correction parameters, for example by manipulating the image frames following a correction algorithm or software and using the processing information extracted externally by the processing unit 153.

The image corrector does not need to be specifically at the display side, and it can be placed anywhere so as to receive image frames from the image pickup unit 115 and processing information from the processing unit 153. For example, such image corrector 112 may be part of a CCU 5153 as described with reference to FIG. 1, or it may be included in the distribution node 104.

The image corrector 112 may perform various image processes for an image frame, for example in the form of RAW data, transmitted thereto from the image pickup unit 115. These image processes include various known signal processes such as, for example, a development process, and/or an enlargement process (electronic zooming process Processes such as image quality improving process (a bandwidth enhancement process, a super-resolution process, a noise reduction (NR) process and/or an image stabilization process) can be done based on the processing information, e.g. correction parameters, obtained by the external processing unit 153. Other processes, such as autofocus, autoexposure or auto-white balance can be done in the image corrector 112 based on the image frame or based on data and processing information, e.g. correction parameters, received from the external processing unit 153.

Thus, a real-time display of the image frames is combined with corrections which may have a small delay. A first image frame may be displayed, from which processing information, e.g. a correction parameter, is derived externally, and the processing information, e.g. correction parameter, is applied to subsequently displayed image frames after the first displayed image frame. This does not disturb the surgery process or the surgeon hand-eye coordination. In some embodiments, the delay of the correction can be unnoticeable. For example, the corrections can be made at a faster speed than the motions of the image pickup unit and of the surgery equipment. Extracting the processing information, e.g. correction parameter, is usually the process that requires most of the computing load, and it can be done outside the operating theater, using image frames and image data obtained in the operating theater.

Further, the image receptor 113 (for example, the display 114) may include a Graphic User Interface (GUI) for performing various operations for display on a display apparatus, such as swap, flip, color adjustment, contrast adjustment and switching between different perspectives (e.g. between 2D and 3D displays). In embodiments of the present invention, some adjustments, such as flip and color or contrast adjustment, may be automatically done as part of the image correction, with little latency, thanks to the processing unit 153.

Data communication exists between the image pickup unit 115 and the image receptor 113. Data communication also exists between the image pickup unit 115 and the processing unit 153, as well as between the processing unit 153 and the image receptor 113. The data communication can be provided by data transmission means, such as connections 101, 102, 103. For example, wireless connections can be provided. Preferably, wired connections are used, such as optical connectors, data buses, data cables, and the like. If optical connections are used for sending optical data signal between the different units and receptors, a photo-electric conversion module for converting an optical signal into an electric signal may be provided in the different units.

In preferred embodiments, at least the data sent from the processing unit to the image receptor is electronic data. Preferably, the connections may form a data network which preferably introduces little or no appreciable delay. Known elements of local area networks (network adapters, network medium such as shielded or unshielded cables, cable ports, splitters, and the like) can be used to provide connection between the different elements of the system.

Figure 3:
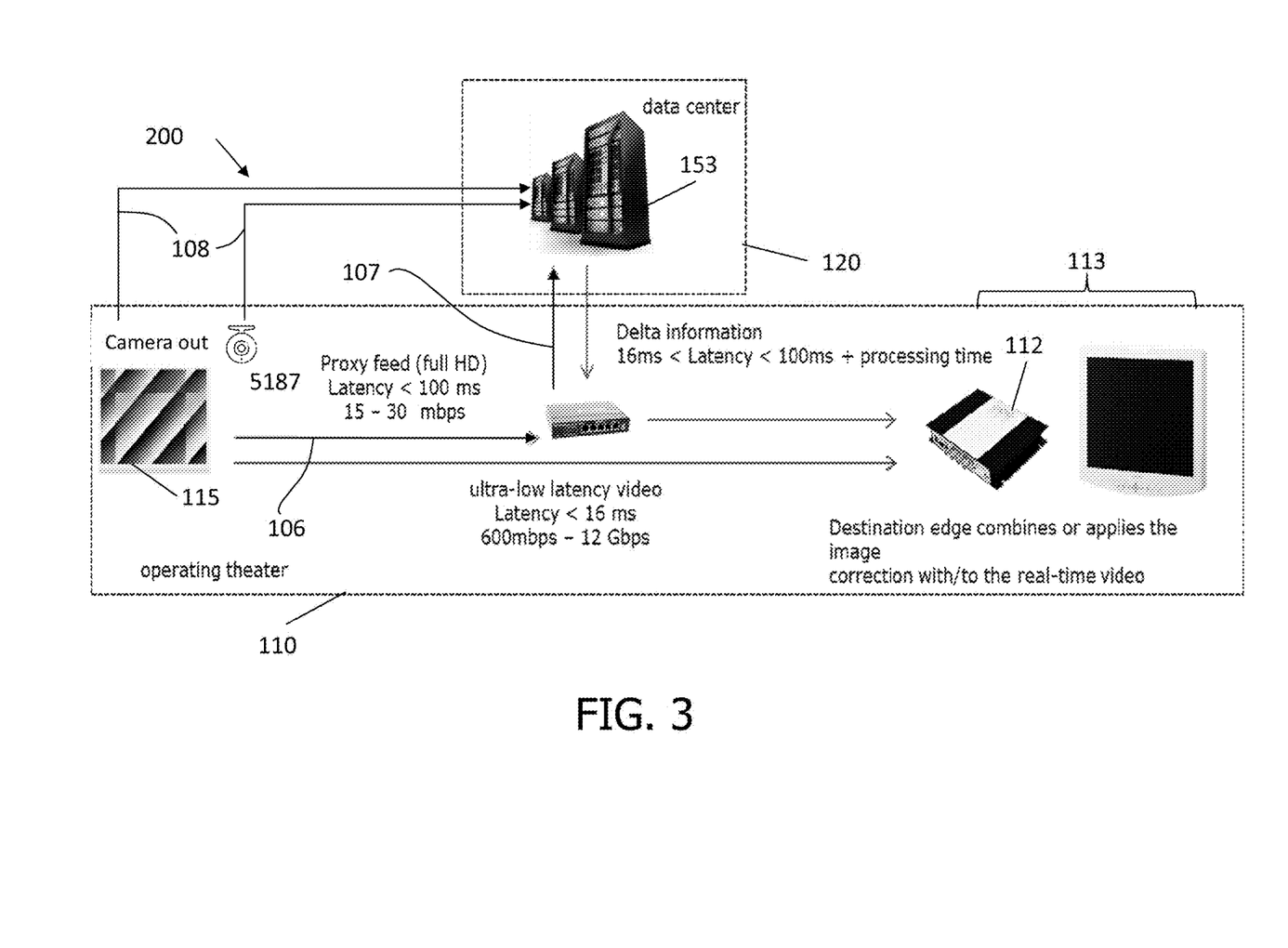
FIG. 3 is a view illustrating an example of a distributed image processing according to further embodiments of the present invention.

In some embodiments, a distribution node 104, as shown in FIG. 2 and FIG. 3, can be included. The distribution node 104 may be a network switcher or a network control manager. In some embodiments, the distribution node 104 may receive data including processing information, e.g. correction parameters, from the processing unit 153 outside the operating theater 110, and sends the data to the image receptor 113. In the particular embodiment shown in FIG. 2, the image pickup unit 115 is able to feed image frames directly to the image receptor 113, and image frames and/or image data directly to the processing unit 153 at the data center 120. This can be done via connections 102, 103 as described before, for instance including a splitter for sending the information to the processing unit 153 and the image receptor 113.

Figure 5:
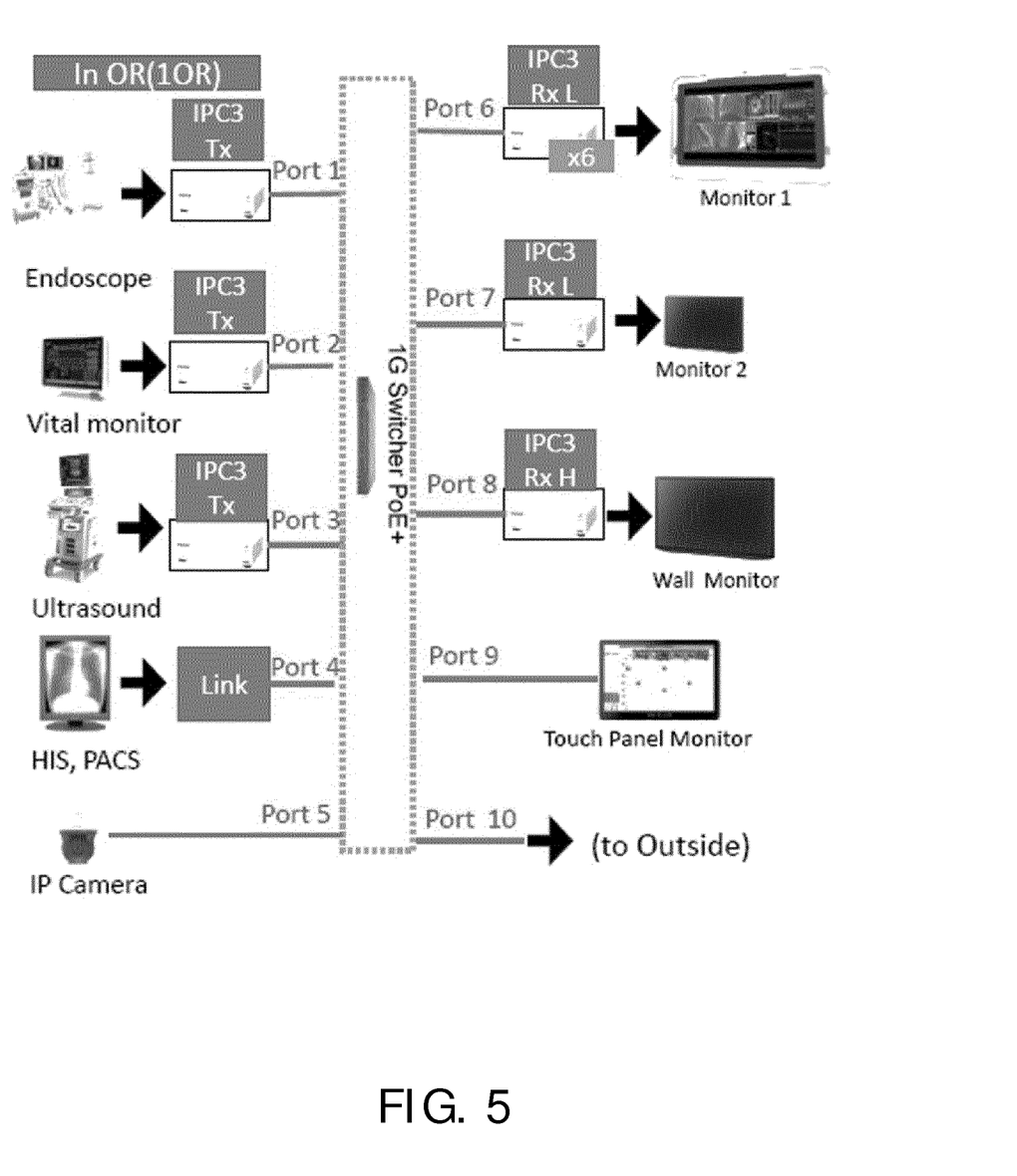
FIG. 5 illustrates imaging data input devices and output devices interconnected as can be used in embodiments of the present invention.

In the alternative embodiment shown in FIG. 3, the system 200 includes a distribution node 104 which also receives image frames (and optionally image data, not shown), from the image pickup unit 115 via a connection 106, and sends them to the processing unit 153, via a further connection 107. As before, the image pickup unit 115 can directly feed image frames to the image receiver 113 via a connection 102, but the communication between the image pickup unit 115 and the processing unit 153 is not a direct connection, but performed via the distribution node 104. An example thereof is also shown in FIG. 5, illustrating different input means, different output means and a distribution node, being a gigabit switcher. With direct connection it is meant a means of direct data transfer between two units via a single transmitting medium, such as one cable, without intermediate nodes which may increase further the latency.

The latency may be under 100 milliseconds at 15 to 30 Mbps (mega-bit per second) in the proxy feed between the image pickup unit 115 and the distribution node 104 and the node 104 and the processing unit 153. The image correction, and/or the processing information, e.g. correction parameters, can be provided with minimum delay. In the case of FIG. 3, the delay of the data transmission (including processing information) depends on the processing time and the latency, which falls between for example 16 ms and 100 ms. However the latency of image frame transmission between the image pickup element 115 and the image receptor 113 is very small, for example under 16 ms at 600 Mbps to 12 Gbps, through a direct connection 102.

In the embodiment of FIG. 2, the processing unit 153 receives raw image frames from the image pickup element 115, and analyzes and extracts at least one processing information which can be sent to the image receptor 113, which performs the correction on the further image frames received from the image pickup unit 115.

In embodiments of the present invention, as shown in FIG. 3 (but which can be equally applicable to the embodiment of FIG. 2), the processing unit 153 may receive separate image data related to the conditions of image acquisition, via further connections 108. The image data may be obtained from the image pickup element 115, from the image frames (e.g. as metadata of the image frames), from sensors sensing parameters of the operating devices, from further image pickup units 5187 at the operating theater, etc. or from other types of sensors. Processing information, e.g. correction parameters, are extracted from the image data and from the frames by the processing unit 153. These parameters are sent to the image receptor 113, or specifically to its image corrector 112 which may perform the correction on any further image frames received from the image pickup unit 115, as explained before.

The present invention can be applied to parts of the system shown in FIG. 1. For example, another example of image data may include illumination conditions of the surgical region of a patient. FIG. 1 shows that the light source apparatus 5157 includes a light source such as, for example, a light emitting diode (LED) or a laser source, and supplies irradiation light for imaging of a surgical region to the endoscope 5115. In embodiments of the present invention, the intensity and wavelength (color) of the light emitted by the light source using LED or laser, or VCSEL can be used as image data, and sent to the processing unit 153. The image data can be collected with a sensor or directly from the light source apparatus.

Although the distribution node is shown in FIG. 2 and FIG. 3, the present invention is not limited by the presence of a distribution node 104, and the connections between the image receptor 113 and the processing unit 153 may be a direct connection, or may include a splitter or the like.

Example 1—Rotation Compensation

A system according to embodiments of the present invention can be applied to rotation compensation in endoscopy. The processing unit 153 may receive image frames, and the angle of rotation of the camera of an endoscope acting as image pickup unit 115, with respect to a predetermined baseline, can be extracted. This can be accomplished, for example, with an algorithm that tracks an object in the image, and calculates the rotation angle of this object. This angle is sent to the image receptor 113 as a compensation or correction parameter. The image receptor 113 receives low latency video stream as image frames from the image pickup unit, as well as the rotation angle as compensation or correction parameter, and rotates the low latency video stream over this angle, but in the opposite direction, to stabilize the horizon of the image.

It is to be noted that in this case, the correction parameter is extracted from the image frames, which simplifies the number of elements and computing. However, the present invention is not limited to this, and in embodiments the processing unit may additionally or instead receive external input, for example image data including data regarding the conditions in which the image is being taken. The image data can be obtained by a sensor or the like which directly detects (e.g. mechanically or optically) the rotation of the endoscope.

In any case, as a result, in the present Example 1 a counter rotation is applied with a small delay, so the angle obtained in a frame is compensated in a subsequent frame, but the display of image frames (e.g. video stream) itself does not suffer from any additional latency of the analysis done on the processing unit 153.

Example 2—Color Analysis in Combination with Image Quality Enhancement Processor A system according to embodiments of the present invention can be applied to image quality enhancement processor in a general image and video source, including endoscopy. The processing unit 153 receives an image frame from an image pickup unit 115 and analyzes the colors in the image to determine which image quality enhancement parameters are appropriate (e.g. best suited) to display the image on the monitor acting as a display 114. These parameters can include color matrix information for color correction of the image, or degree of noise reduction, and other information related to image processing. The image quality enhancement parameters are sent to the image receptor 113 as correction parameters. The image receptor 113 receives the image quality enhancement parameters and subsequent image frames from the image pickup unit 115, and sends the corresponding commands to a display (e.g. a monitor) to apply these image quality enhancement parameters to the frames.

As a result, the system automatically applies appropriate image quality enhancement parameters to the image, and in case the content of the image changes during surgery, the monitor will automatically adjust the image quality enhancement settings.

Although the present aspect has been described with reference to the full system, the present invention also relates to a processing unit configured for performing the actions as described above in the processing system, as well as to an image receptor configure for performing the actions as described above in the processing system.

In another example, image analysis and annotation is performed. In this example, the processing unit 153 received image including a particular anatomical site or anatomical landmark (e.g. position of vessel, tumor, surgical devices for example forceps), and recognize positions of such anatomical landmark. This recognition can be performed by machine learning based algorithm or normal pattern recognition. Then the processing unit 153 send position information and/or annotation image for superposing on the image, to the image receptor 113. As such recognition process requires high amount of computing resource and updated database as reference data, there is a great advantage of being performed at the data center (the processing unit 153) side.

The other example is image stabilization.

In this case, at the image processor 153, global motion vectors of the image are detected and stabilization parameters are provided to the image receptor.

In a second aspect, the present invention provides a method of distributing and processing images, for example images related to surgery. The method includes obtaining an image frame, and subsequently sending the image frame to an image receptor as well as separately processing that image frame, thereby extracting at least one correction parameter. The method further includes applying the correction parameter extracted from an image frame to any subsequently obtained image frames.

Although the correction is applied with a delay on obtained image frames, using correction parameters obtained from previous image frames, the display is not delayed (e.g. the video stream does not suffer latency).

In the case there is no previous image frame, the image is displayed without reflecting any correction or processing result first. Once the correction parameters are provided with the certain delay, the correct image is displayed. Thus, while minimum required image (original image from the endoscope) is maintained to display without delay, as soon as the correction or processing parameters are available, the displayed image is enriched.

The correction will have an acceptable quality because detectable changes in viewing conditions do not change faster than processing time. Moreover, correction parameters can be adapted continuously using the newly obtained image frames.

Figure 4:
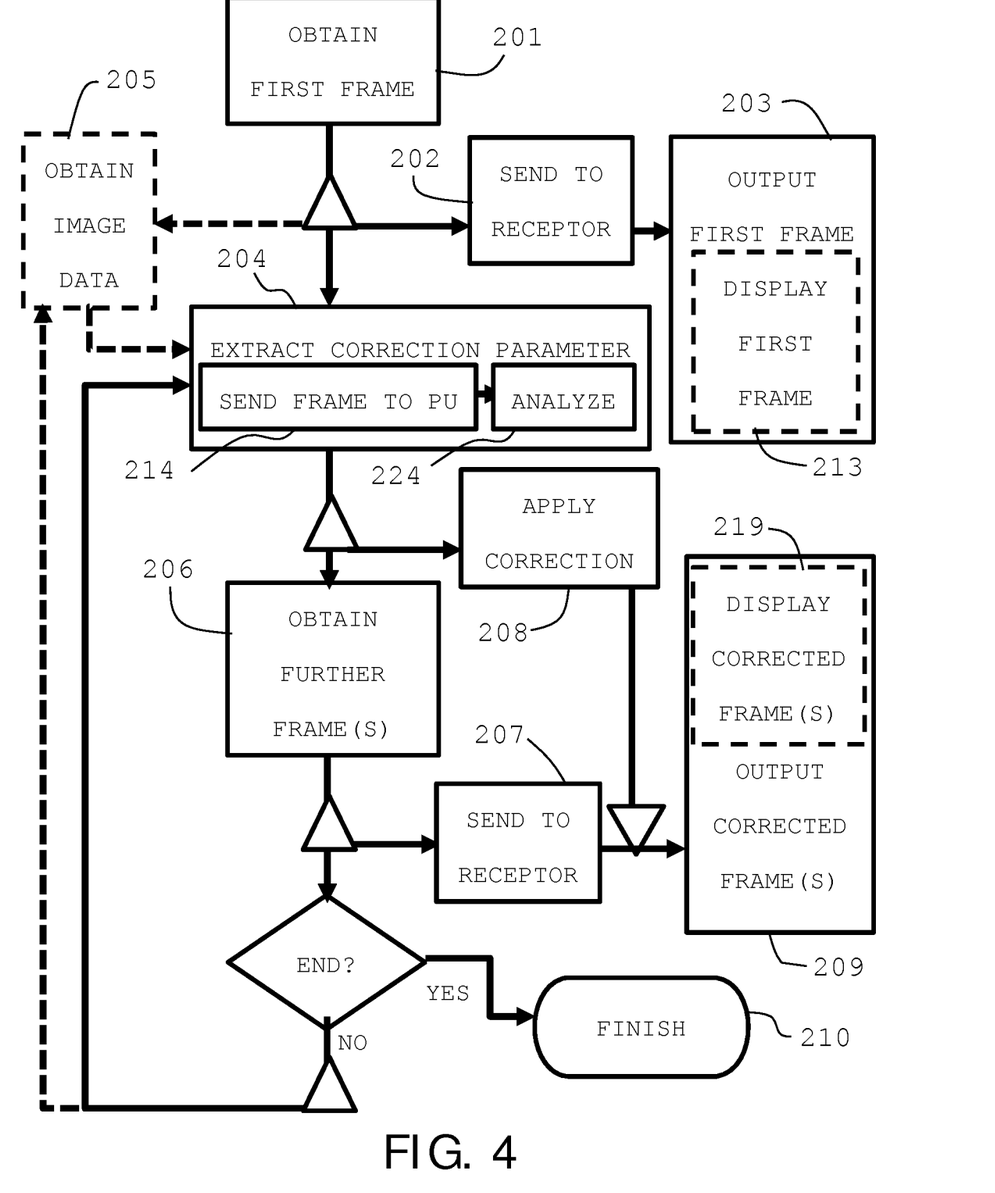
FIG. 4 is a block diagram depicting an example of a method of image analysis and correction according to embodiments of the present invention.

FIG. 4 shows a process, including optional steps with dashed lines, according to embodiments of the present invention. In a first step, the method comprises obtaining 201 a first image frame and sending 202 it to an image receptor, where it can be output, for example by displaying 203 the first image frame. A further step, which may be simultaneous to the step of sending 202 the image to the receptor, comprises extracting 204 at least one correction parameter, which may include sending 214 the image frame to an external processing unit 153 and analyzing 224 the frame to extract the correction parameter. This can be done by an algorithm, program or dedicated software in the processing unit, depending on the type of correction desired.

Optionally, the method may include obtaining 205 further image data related, for example, to the conditions under which the image frame has been obtained. This additional image data can be used to extract the correction parameter, for example together with the analyzing 224 the image frame.

Subsequently, the method comprises obtaining 206 a further image frame, and sending 207 it to an image receptor. A corrected image frame is obtained by applying 208 the previously extracted correction parameter, corresponding to the previous frame, to the further frame. This can be done by sending the correction parameter to a register in the image receptor, and applying the correction parameter by manipulating the next image frame arriving to the image receptor. The manipulation can be done with an image corrector, which was described with reference to the first aspect of the present invention.

The corrected image frame can be sent 209 to an output, for example the method may comprise displaying 219 the corrected frame. Thus, there is no need to process the further image frame in order to extract a correction parameter, as the correction parameter was extracted from the previous frame.

While the further frame is sent to the receptor, corrected and possibly displayed, the method may comprise extracting a new correction parameter, optionally obtaining image data, which will be used to correct any subsequent frame. The process will continue for as long as it is desired. When the visualization stops, the process can be finalized 210.

The present invention is not limited by the method described with reference to FIG. 4. For example, several frames may be displayed with no correction (first frames) before obtaining the first correction parameters to apply to subsequent image frames. Additionally or alternatively, the at least one correction parameter may be extracted from some image frames, but not from others; for example, the step of extracting the correction parameter may be skipped for a predetermined number of frames, thus reducing computing resources and lag. The processing time and transmission latency can be compared to the frame rate of the display, in order to set an appropriate number of skipping frames so that the quality of the image is not negatively affected. For example, if the video stream has a frame rate of 30 fps, and the latency is approximately 40 ms, extracting the correction values can be done each two frames.

The present invention provides separation of image frame analysis and extraction of correction parameters from the display of images, which is performed with very small latency, much smaller than the processing time and transmission latency. Moreover, there is no need to transmit a corrected image from the processing unit 153 to the image receptor 113, because the image correction can be provided in the image receptor 113, and only correction parameters need to be transmitted from the processing unit to the image receptor 113. This reduces the size of data packages transmitted through the connection 101, which may be wired or wireless, between the processing unit 153 and the image receptor 113.

Although the explanation was made based on an endoscopic image, the present invention is not limited to endoscopic images, and other types of image sources can be used, i.e. a surgical microscopic image, an image from an exoscope, an image from a surgical camera or a surgical room camera, . . . can be used.

In summary, the present invention provides video, image, and data processing techniques which do not introduce latency on the video stream used by the surgeon to operate on the patient. Moreover, computing power can be offloaded to machines located in a data room with appropriate cooling and maintenance procedures.

The following numbered paragraphs provide further example aspects and features of the present technique:

Paragraph 1. A processing system (100, 200) for processing surgical images, the system including:
- at least one image pickup unit (115) for obtaining surgical image frames and data,
- at least one image receptor (113) for receiving surgical image frames to be displayed,
- a processing unit (153) connected with a network (103, 106, 107) to the image pickup unit (115) for receiving surgical image frames, the processing unit (153) being configured for processing the surgical image frames and for extracting at least one processing information thereof, wherein the processing unit further is being connected to the at least one image receptor (113) for providing the at least one correction parameter to the at least one image receptor, and wherein the system further comprises a connection (102) between the at least one image pickup unit (115) and the image receptor (113), for sending the surgical image frames directly to the image receptor (113).

Paragraph 2. The processing system (100, 200) of the previous paragraph wherein the processing unit (153) is an external processing unit positioned outside an operation theater separated from the at least one image pickup unit (115) and the at least one image receptor (113) positioned inside the operation theater.

Paragraph 3. The processing system (100, 200) of the previous paragraph wherein the processing unit (153) is adapted to provide a correction parameter from surgical image frames and further image data, the processing unit further including input for receiving further image data.

Paragraph 4. The processing system of any of the previous paragraphs wherein the at least one image receptor (113) includes means (112) for applying at least one correction parameter to image frames.

Paragraph 5. The processing system of any of the previous paragraphs wherein the at least one image pickup unit (115) comprises a surgical video input and the image frames comprise a surgical video stream.

Paragraph 6. The processing system of any of the previous paragraphs wherein the image receptor (113) includes a display (114) for displaying surgical image frames.

Paragraph 7. The processing system of any of the previous paragraphs wherein the at least one image pickup unit (115) comprises an endoscope.

Paragraph 8. The processing system according to any of the previous paragraphs, wherein the system is connected via Gigabit Ethernet.

Paragraph 9. The processing system according to any of the previous paragraphs, wherein image data transmitted in the system is transmitted in a slice based transmission mode.

Paragraph 10. The processing system according to any of the previous paragraphs, wherein image data transmitted in the system is compressed prior to transmission.

Paragraph 11. A method for processing images comprising
- obtaining (201, 206) surgical image frames,
- sending (202, 207) at least one surgical image frame to an image receptor,
- separately processing the at least one surgical image frame thereby extracting (204) at least one correction parameter,
- subsequently correcting any further surgical image frames sent to the image receptor by applying (208) the at least one correction parameter to the any further surgical image frames.

Paragraph 12. The method of paragraph 11 further comprising displaying (219) the surgical image frames received in the image receptor Paragraph 13. The method of paragraphs 11 or 12 further comprising obtaining (205) image data, and wherein processing the surgical image frames and extracting (204) at least one processing information comprises processing the surgical image frames and image data related to the conditions of obtaining surgical image frames.

Paragraph 14. The method of any of paragraphs 11 to 13 wherein obtaining surgical image frames comprises obtaining a surgical video stream.

Paragraph 15. The method of any of paragraphs 11 to 14 wherein extracting (204) at least one processing information includes extracting any or all of color correction, contrast correction, illumination information, displacement and image rotation.

Paragraph 16. A processing unit (153) for processing surgical images, the processing unit (153) being configured for receiving surgical image frames and data from at least one image pickup unit (115) for obtaining surgical image frames and data, processing the surgical image frames and for extracting at least one processing information thereof, and providing the at least one processing information to at least one image receptor for applying said at least one processing information to surgical image frames received by the at least one image receptor directly from the at least one image pickup unit (115).

Paragraph 17. An image receptor (113) for receiving surgical image frames to be displayed, the image receptor (113) being configured for receiving surgical image frames directly from at least one image pickup unit (115) and for receiving an at least one processing information determined by a processor based on surgical image frames received from said at least one image pickup unit (115), the image receptor (113) being configured for applying the at least one processing information to the surgical image frames received directly from the at least one image pickup unit (115).

The invention claimed is:

1. A processing system for processing surgical images, the system including:
- at least one image pickup unit for obtaining surgical image frames and data,
- at least one image receptor for receiving surgical image frames to be displayed,
- a processing unit connected with a network to the image pickup unit for receiving surgical image frames, the processing unit being configured for processing the surgical image frames and for extracting at least one processing information thereof, wherein the processing unit further is being connected to the at least one image receptor for providing the at least one correction parameter to the at least one image receptor, and wherein the system further comprises a connection between the at least one image pickup unit and the image receptor, for sending the surgical image frames directly to the image receptor.

2. The processing system of claim 1 wherein the processing unit is an external processing unit positioned outside an operation theater separated from the at least one image pickup unit and the at least one image receptor positioned inside the operation theater.

3. The processing system of claim 2 wherein the processing unit is adapted to provide a correction parameter from surgical image frames and further image data, the processing unit further including input for receiving further image data.

4. The processing system of claim 1 wherein the at least one image receptor includes means for applying at least one correction parameter to image frames.

5. The processing system of claim 1 wherein the at least one image pickup unit comprises a surgical video input and the image frames comprise a surgical video stream.

6. The processing system of claim 1 wherein the image receptor includes a display for displaying surgical image frames.

7. The processing system of claim 1 wherein the at least one image pickup unit comprises an endoscope.

8. The processing system according to claim 1, wherein the system is connected via Gigabit Ethernet.

9. The processing system according to claim 1, wherein image data transmitted in the system is transmitted in a slice based transmission mode.

10. The processing system according to claim 1, wherein image data transmitted in the system is compressed prior to transmission.

11. A method for processing images comprising
obtaining surgical image frames,
sending at least one surgical image frame to an image receptor,
separately processing the at least one surgical image frame thereby extracting at least one correction parameter,
subsequently correcting any further surgical image frames sent to the image receptor by applying the at least one correction parameter to the any further surgical image frames.

12. The method of claim 11 further comprising displaying the surgical image frames received in the image receptor.

13. The method of claim 11 further comprising obtaining image data, and wherein processing the surgical image frames and extracting at least one processing information comprises processing the surgical image frames and image data related to the conditions of obtaining surgical image frames.

14. The method of claim 11 wherein obtaining surgical image frames comprises obtaining a surgical video stream.

15. The method of claim 11 wherein extracting at least one processing information includes extracting any or all of color correction, contrast correction, illumination information, displacement and image rotation.

16. A processing unit for processing surgical images, the processing unit being configured for
receiving surgical image frames and data from at least one image pickup unit for obtaining surgical image frames and data,
processing the surgical image frames and for extracting at least one processing information thereof, and
providing the at least one processing information to at least one image receptor for applying said at least one processing information to surgical image frames received by the at least one image receptor directly from the at least one image pickup unit.

17. An image receptor for receiving surgical image frames to be displayed, the image receptor being configured for receiving surgical image frames directly from at least one image pickup unit and for receiving an at least one processing information determined by a processor based on surgical image frames received from said at least one image pickup unit, the image receptor being configured for applying the at least one processing information to the surgical image frames received directly from the at least one image pickup unit.

* * * * *